United States Patent
Okuda et al.

(10) Patent No.: US 8,500,824 B2
(45) Date of Patent: Aug. 6, 2013

(54) KNEE JOINT INCLUDING MANUAL LOCK MECHANISM AND ARTIFICIAL THIGH

(75) Inventors: Masahiko Okuda, Hyogo (JP); Yoshiaki Nakaya, Hyogo (JP)

(73) Assignee: Nabtesco Corporation, Tokyo (JP)

( * ) Notice: Subject to any disclaimer, the term of this patent is extended or adjusted under 35 U.S.C. 154(b) by 54 days.

(21) Appl. No.: 12/919,863

(22) PCT Filed: Mar. 7, 2008

(86) PCT No.: PCT/JP2008/054178
§ 371 (c)(1), (2), (4) Date: Aug. 27, 2010

(87) PCT Pub. No.: WO2009/110097
PCT Pub. Date: Sep. 11, 2009

(65) Prior Publication Data
US 2011/0009981 A1    Jan. 13, 2011

(51) Int. Cl.
*A61F 2/64* (2006.01)
(52) U.S. Cl.
USPC ........................................................... 623/44
(58) Field of Classification Search
USPC ..................................................... 623/39–45
See application file for complete search history.

(56) References Cited

U.S. PATENT DOCUMENTS

| | | | |
|---|---|---|---|
| 3,663,967 A * | 5/1972 | Vermillion | ................ 623/31 |
| 4,458,367 A | 7/1984 | May | |
| 4,756,713 A | 7/1988 | Cooper | |

FOREIGN PATENT DOCUMENTS

| | | |
|---|---|---|
| GB | 2099708 A | 12/1982 |
| GB | 2181357 A | 4/1987 |
| JP | 58-001444 A | 1/1983 |
| JP | 62-087149 A | 4/1987 |
| JP | 09-075382 | 3/1997 |
| JP | 2001-137268 | 5/2001 |
| JP | 2002-058689 | 2/2002 |

\* cited by examiner

*Primary Examiner* — Bruce E Snow
(74) *Attorney, Agent, or Firm* — Frommer Lawrence & Haug LLP; Ronald R. Santucci

(57) ABSTRACT

The disclosure relates to a technology of a manual lock mechanism for manually switching over the oscillating motion of an upper member and a lower member at a knee joint between a locked condition and an unlocked condition. More particularly, the disclosure aims at a simple structure of the manual lock mechanism and a size reduction of the knee joint or an artificial leg including the manual lock mechanism. For these purposes, one of oscillating shafts for swingingly coupling the upper and lower members is regulated. Therefore, the manual lock mechanism includes an oscillating shaft including an irregular part and a lock member for regulating the movement of the oscillating shaft. The lock member can be switched over between a locked condition where the lock member is in contact with the irregular part of the oscillating shaft and the unlocked condition where it is separate from the irregular part. When the lock member is in the locked condition, force from the oscillating shaft is applied as compression load in the longitudinal direction of the lock member.

12 Claims, 9 Drawing Sheets

KNEE JOINT INCLUDING MANUAL LOCK MECHANISM AND ARTIFICIAL THIGH

This application is a 371 of PCT/JP2008/054178 filed on Mar. 7, 2008 published on Sep. 11, 2009 under publication number WO 2009/110097 A.

This invention relates to a knee joint capable of manually switching over an upper member located at an upper side of the knee and a lower member located at a lower side of the knee between an unlocked condition where the upper and lower members are swingable and a locked condition where they are unswingable when the knee is in its extended condition and an artificial thigh including the knee joint. More particularly, the invention relates to a technology for effectively achieving a size reduction of a manual lock mechanism for switching over the upper and lower members between the unlocked condition and the locked condition.

BACKGROUND ART

The knee joint functions as a knee capable of swinging an upper member and a lower member. One representative example of an artificial leg including such a knee joint is an artificial thigh (or an above knee prosthesis). The artificial leg including the knee joint normally comprises a resistance force (or a drag) generating means, such as a pneumatic cylinder, a hydraulic cylinder or a spring cylinder, for effectively performing swinging motion. From the standpoint of size reduction or simple structure of the artificial leg, the hydraulic cylinder and the spring cylinder are more preferable than the pneumatic cylinder. On the other hand, the pneumatic cylinder has such a feature that a repulsive force can be obtained after the knee is bent maximum.

For example, Patent Document 1 discloses an artificial leg including a pneumatic cylinder; Patent Document 2, an artificial leg including a hydraulic cylinder; and Patent Document 3, an artificial leg including a spring cylinder, respectively.

Patent Document 1: Japanese Patent Laid-Open Gazette No. 2001-137268

Patent Document 2: Japanese Patent Laid-Open Gazette No. 2002-58689

Patent Document 3: Japanese Patent Laid-Open Gazette No. 1980-130657

Since the artificial leg including the knee joint has an upper and a lower member which are swingable, prevention of any accidental knee bending is desirous for its wearer. Patent Document 4 shows a technology for preventing knee bending wherein swinging motion is automatically locked/unlocked at walking by generating a braking effect in accordance with application of the wearer's load.

Patent Document 4: Japanese Utility Model Publication Gazette No. 1980-32574

However, since such a technology for preventing knee bending uses the wearer's load, it cannot be effectively applied, for example, to a case where the wearer walks on a snow-covered road or an uneven ground. In order to reliably prevent accidental knee bending at walking on a snow-covered road or an uneven ground, a locked condition should be achieved when the knee is in an extended condition. The expression "the knee-extended condition" refers to a state wherein the upper and lower members are extended straight (Patent Documents 5 and 6) and a state wherein the upper and lower members are bent in a dogleg shape (Patent Document 7).

Patent Document 5: Japanese Patent Laid-Open Gazette No. 1987-87149

Patent Document 6: GB2099708A

Patent Document 7: Japanese Patent Laid-Open Gazette No. 1997-75382

DISCLOSURE OF THE INVENTION

Problem to be Solved by the Invention

According to the technologies of the Patent Documents 5 through 7, accidental knee bending, in the locked condition, can reliably be prevented at walk on a snow-covered road or an uneven ground. Moreover, the swinging motion of the upper and lower members can also be temporarily manually switched over from the locked condition to the unlocked condition. Accordingly, if the wire is fixed in a tensioned condition in order to normally achieve an unlocked condition, it can be considered that an appropriate swinging motion can also be met at the time when a normal walking is conducted. However, the construction of the conventional manual lock mechanism is complicated and many component parts are required. Moreover, a mechanism for fixing the state of the wire in its tensioned condition is additionally required. Therefore, difficulty is encountered in an effort for achieving a size reduction of the knee joint and artificial leg. Moreover, there is room for improvement on the appearance.

It is, therefore, an object of the present invention to provide a technology for achieving a simple structure of a manual lock mechanism capable of selectively switching over a locked condition and an unlocked condition at walk and achieving a size reduction of a knee joint and an artificial leg including the manual lock mechanism just mentioned.

Another object of the present invention is to provide a technology in which the appearance is excellent and operability for switching a manual lock mechanism is enhanced.

Other objects of the invention will become manifest upon reading the description to follow.

Means to Solve the Problem

The inventors of the present invention paid attention to that the coupling means for swingably coupling the upper and lower members includes the oscillating shaft, and thought that a locked condition can be obtained by restricting the movement of the oscillating shaft. The oscillating shaft is essentially required for a knee joint and an artificial leg. By using the oscillating shaft as one of the component elements of the manual lock mechanism, the inventors aim at a simple structure of the manual lock mechanism.

The manual lock mechanism of the present invention has the following features;

(A) the oscillating shaft is one of the component elements of the manual lock mechanism and includes an irregular part extending in an axial direction thereof;

(B) the manual lock mechanism includes a lock member supported by one of the upper and lower members by which the oscillating shaft (that is, the oscillating shaft as an object whose movement is restricted) is rotatably supported, and the lock member can be manually selectively switched over between a locked condition of being in contact with the irregular part and an unlocked condition of being separate from the irregular part; and (C) a first end part of the lock member in the longitudinal direction is in face-to-face contact with the irregular part in the locked condition so that the upper and lower member prevent the knee from bending.

When the locked condition is kept, a considerable amount of force is applied to the lock member for suppressing the swinging motion. This force is normally applied as a bending load in the conventional lock member. Therefore, sufficient consideration is required to pay to the strength design of the lock member. In the manual lock mechanism of the present invention, when the locked condition is kept, force from the oscillating shaft is applied as a longitudinal compression load to the lock member. Since the load is a compression load, a sufficient degree of freedom can be reserved in the strength design of the lock member. Moreover, since the lock member can be arranged horizontally, the manual operating part can be disposed at the second end part opposite to the first end part which contacts the oscillating shaft. Since the lock member can be selectively manually switched between the unlocked condition and the locked condition, the wearer can walk in the locked condition or in the unlocked condition.

As a coupling means for swingably coupling the upper and lower members, there is a single axis where the center of oscillation is constant or a multi-axis where the center of oscillation is changed in accordance with the oscillating motion. With one having a single axis, movement of only one single-axis is restricted and with one having a multi-axis, movement of one of the plural oscillating shafts is restricted. Since only one single-axis is located at an upper part of the knee joint, the wearer of the artificial leg including this knee joint can operate the outer-side second end part (i.e., the manual operating part) opposite to the inner-side first end part facing the single-axis by himself and can easily switch over to the locked condition or the unlocked condition in accordance with necessity. With the multi-axis including the plural oscillating shafts, the oscillating shaft located at an upper part of the knee joint is restricted so that the same switching-over operation can be performed as in the single-axis. Therefore, the oscillating shaft located at an upper part of the knee joint is preferably restricted, and in that case, the lock member is most preferably supported on the socket attaching part having a sufficient mechanical strength.

Here, the mode (or condition) for locking the oscillating motion between the upper member and the lower member by restricting the movement of the oscillating shaft is the mode where the knee is extended by the upper and lower members. In other words, this mode is a mode for enabling the wearer of the artificial leg to walk on a snow-covered road or an uneven ground. Therefore, this mode is in a range of knee angles from 0° where the upper and lower members are extended straight to 20° where no difficulty is felt by the wearer to walk.

The lock member is shifted between the locked position and the unlocked position in accordance with the operation for switching over to the locked condition or the unlocked condition. Therefore, it is preferable to provide a position regulating means for regulating the position in such a manner as to keep the locked condition or the unlocked condition. As one example of the position regulating means, there is a method for removably dropping a position regulating bolt or pin in a groove having a small depth or a method for utilizing the catching function of a pawl.

The lock member can be switched over to the locked condition or the unlocked condition by rotating operating or sliding operation. For both the rotating operation and sliding operation, the movement caused by this switching-over operation is a movement in a horizontal plane of the lock member horizontally disposed. Therefore, only a small space is required for the lock member and for movement thereof.

This type knee joint and an artificial leg including the same is preferably provided with a resistance force (or a drag) generating means for generating a resistance force against bending or extending of the knee by the knee joint in order to effectively performing the movement by the knee joint. Since the manual lock mechanism of the present invention has a simple structure and requires only a small space, no difficulty is encountered with the employment of such resistance force generating means. The resistance force generating means may be one of a hydraulic cylinder, a spring cylinder and a pneumatic cylinder. In the artificial thigh equipped with the resistance force generating means in addition to the manual lock mechanism, the manual lock mechanism and the resistance force generating means are located at an inner side of the contour of the knee joint. Owing to this arrangement, a size reduction and an excellent appearance of the artificial thigh can be achieved.

DESCRIPTION OF REFERENCE NUMERAL

Figure 1:
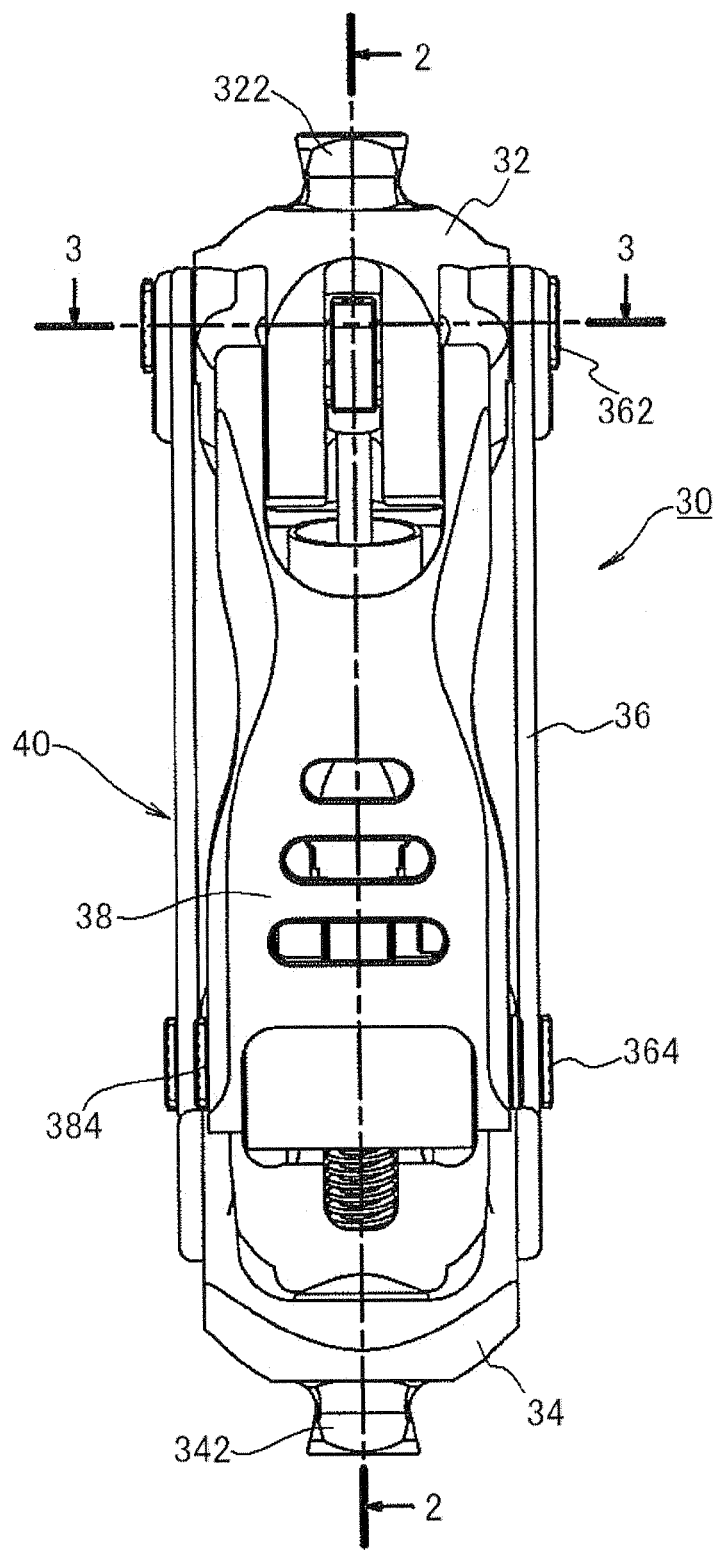
FIG. 1 is a front view showing a first embodiment of a knee joint according to the present invention.

30 . . . knee joint (first embodiment)
32 . . . upper member
34 . . . lower member
36 . . . front-side link
38 . . . rear-side link
40 . . . coupling means
50 . . . extension assisting mechanism
60 . . . hydraulic cylinder
70 . . . manual lock mechanism
72 . . . oscillating shaft
720 . . . irregular part
721 . . . first plane
722 . . . second plane
74 . . . lock member
76 . . . lever (manual operating part)
80 . . . nut member
230 . . . knee joint (second embodiment)
232 . . . upper member
234 . . . lower member
260 . . . pneumatic cylinder
272 . . . oscillating shaft
700 . . . manual lock mechanism (another example)
740 . . . lock member
742 . . . lock pawl
760 . . . push-button type manual operating part
770 . . . stopper

BEST MODE FOR CARRYING OUT THE INVENTION

Figure 2:
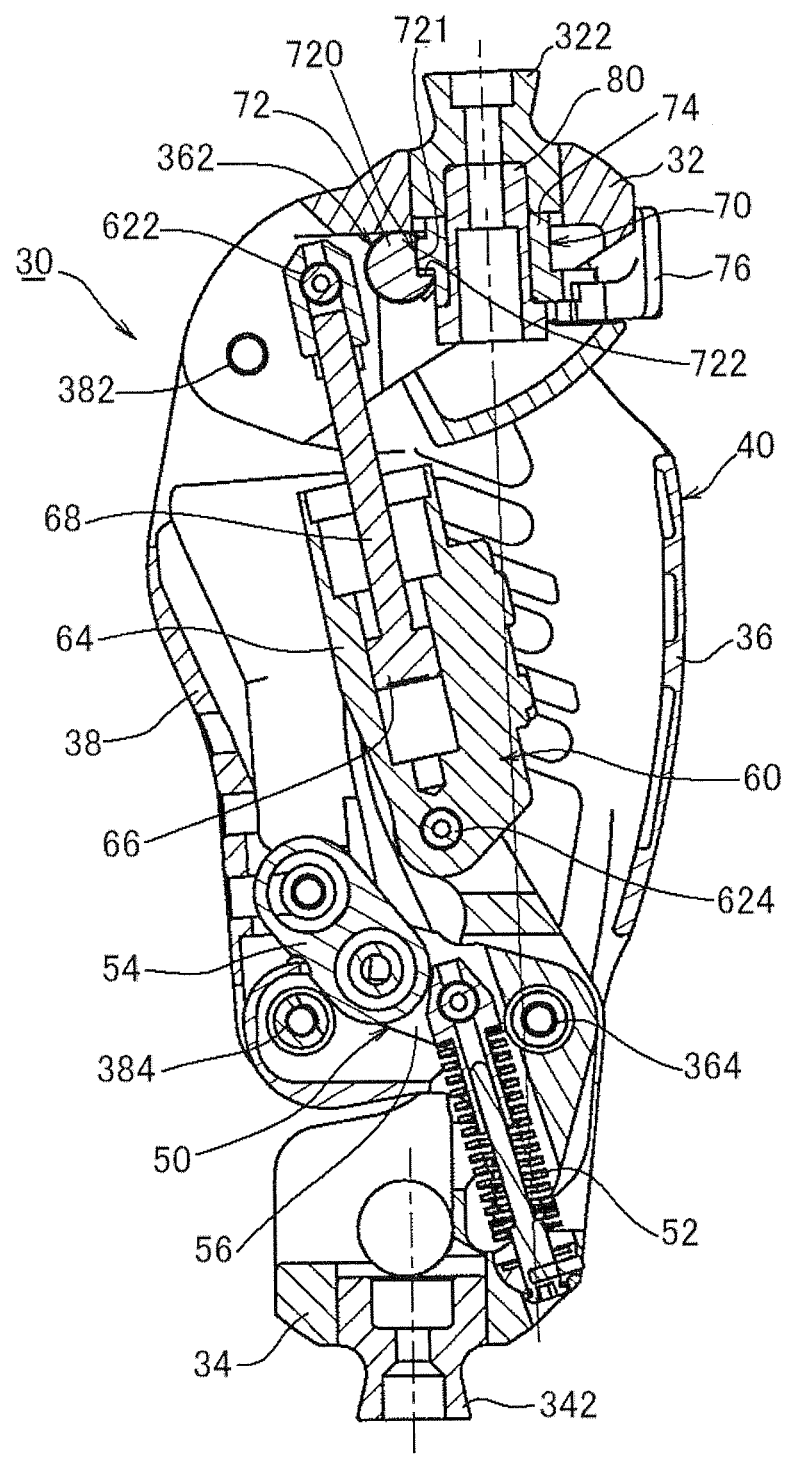
FIG. 2 is a sectional view taken on line 2-2 of FIG. 1.
Figure 3:
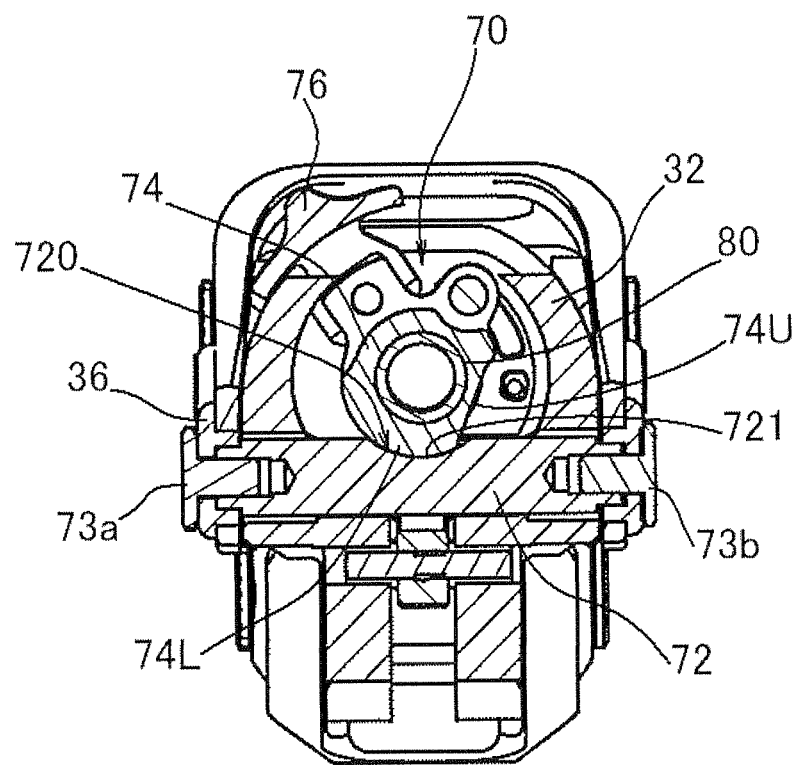
FIG. 3 is a sectional view taken on line 3-3 of FIG. 1.

FIGS. 1 through 3 show a first embodiment in which the present invention is applied to a multi-axis knee joint. A multi-axis knee joint 30 of the first embodiment comprises an upper member 32 located at an upper side of the knee and a lower member 34 located at a lower side of the knee and swingably coupled to the upper member 32 to enable the knee to bend. The upper member 32 integrally supports an alignment block 322 on an upper center part thereof. The alignment block 322 is a part to which a socket, not shown, is attached and supports the artificial leg wearer's load through the thigh inserted in the socket. On the other hand, another alignment block 342 is also disposed at a lower center part of the lower member 34. This alignment block 342 is a part to which a member for supporting a foot part is attached. Therefore, the knee joint 30 constitutes a main part of the artificial thigh.

The multi-axis coupling means 40 swingably couples the upper and lower members 32 and 34. The coupling means 40 is composed of a four-link mechanism. The four-link mechanism is a constraint chain which is formed of four links rotatably connected together. Each of the upper and lower members 32 and 34 functions as one of the four links of the constraint chain. The remaining two links are a front-side link 36 and a rear-side line 38. The two links 36, 38 are provided at upper and lower ends thereof with coupling parts 362, 364; 382, 384 with other links. Each of the front-side and rear-side links 36, 38 has a bilateral symmetrical shape, and the upper and lower coupling parts 362, 364; 382, 384 form a left and right pair, respectively. Therefore, the front-side and rear-side links 36, 38 which are separate in the forward and backward direction cover the outer side of the knee joint in association with each other and define an inside space. An extension assisting mechanism 50 is supported by the knee joint 30 between the lower member 34 and the rear-side link 38. The extension assisting mechanism 50 includes a compression spring 52 and two assisting links 54, 56 and provides an extension force for extending the knee at a stage where the knee bend is small.

A hydraulic cylinder 60 as a resistance force (or a drag) generating means is disposed in the inside space of the knee joint 30. The hydraulic cylinder 60 is rotatably connected to the upper member 32 at an upper attaching position 622 and to the lower member 34 at a lower attaching position 624, respectively, and exerts a resistance force to oscillating motion of the upper and lower members 32, 34. The hydraulic cylinder 60 is known and comprised of a cylinder body 64 having a cylinder hole, a piston 66 for entering the cylinder hole to divide it into two chambers, and a piston rod 68 extending from the piston 66 part to the outside of the cylinder body 64. Since the hydraulic cylinder 60 generates a hydraulic resistance, it includes a known hydraulic circuit, not shown, in the cylinder body 64. The hydraulic circuit comprises a first passage including a first check valve for allowing only a flow from a first chamber on one side of the piston to a second chamber on the other side thereof and a first throttle valve for imparting a flow resistance to this flow; and a second passage including a second check valve for allowing only a flow from the second chamber to the first chamber, and a second throttle valve for imparting a flow resistance to this flow.

The knee joint 30 of the first embodiment comprises a manual lock mechanism 70 for the coupling part 362 which is located in position higher than any other three coupling parts of the coupling means 40 and adjacent to the alignment block 322 having a sufficient mechanical strength. A one-side body of the manual lock mechanism 70 is an oscillating shaft 72 at the coupling part 362. The oscillating shaft 72 is a rotating shaft having a circular shape in section and extending in the horizontal direction, as shown in FIG. 3. The oscillating shaft 72 is secured to the front-side link 36 by set screws 73a, 73b at both ends and rotatably or swingably supports the upper member 32.

The circular oscillating shaft 72 in section is provided at an axial central part thereof with an irregular part 720 formed by digging its own peripheral side surface. The irregular part 720 includes a first plane 721 spreading along the axial direction of the oscillating shaft 72 and a second plane 722 spreading in the direction crossing (generally orthogonal to the first plane 721 in this embodiment) the first plane 721. The first plane 721 of the irregular part 720 extends from the outer periphery nearly to the center of the axis and has an arcuate shape in section along the axial direction. However, the irregular part 720 occupies only a part of an axially central part of the oscillating shaft 72 and its depth (spread of the second plane 722) is very small compared with the shaft diameter (for example, less than ¼ of the shaft diameter). Owing to this arrangement, the oscillating shaft 72 has a large mechanical strength enough to bear the load at the time of oscillating motion and the load at the locked time, in spite that it includes the irregular part 720.

The other-side body of the manual lock mechanism 70 is a lock member 74. The lock member 74, in cooperation with the oscillating shaft 72 including the irregular part 720, realizes a locked condition for suppressing oscillation of the upper member 32 about the oscillating shaft 72 and an unlocked condition for allowing oscillation of the upper member 32. When in the unlocked condition, the lock member 74 is never subject to such a large load as to create a problem of strength. When in the locked condition, however, the lock member 74 directly supports the load of the artificial leg wearer together with the oscillating shaft 72 which restricts movement of the lock member 74 which also restricts movement of the oscillating shaft 72. Therefore, the knee joint 30 is provided with a lock member 74 attached to a portion thereof on which the alignment block 322 as a socket attaching part is supported. The portion on which the alignment block 322 is supported is a part of the knee joint 30 having the largest mechanical strength. In this embodiment, the lock member 74 is attached to the upper member 32 using a supporting bolt (not shown) passing through the center hole of the alignment block 322 and a nut member 80 threadingly engaged with the supporting bolt. The lock member 74 is rotatably supported on the outer periphery of the nut member 80. Owing to this arrangement, the lock member 74 extends in the horizontal direction in such a manner as to cross the oscillating shaft 72 and reaches a second end part located at an outer peripheral edge of the upper member 32 from a first end part supported by the nut member 80.

The first end part of the lock member 74 has a cam shape as shown in FIGS. 2 and 3 and includes a lock part 74L which contacts the irregular part 720 of the oscillating shaft 72 to realize a locked condition, and an unlock part 74U for realizing an unlocked condition separated from the irregular part 20. The second end part located on the opposite side to the first end part when viewed in the longitudinal direction is provided with a lever 76 serving as a manual operating part. The lever 76 is located at an inner side of the contour of the knee joint 30 but at an outer side of the upper member 32. Owing to this arrangement, the artificial leg wearer can switch over to a locked condition or unlocked condition by rotating the lever 76 in accordance with necessity. A positioning member such as a bolt or a pin is attached to a nearby area of the first end part of the lock member 74 so that the positioning member is removably dropped in a guiding groove or positioning groove disposed at the upper member 32 side, thereby constituting a position regulating means for regulating the position of the lock member 74. According to this position regulating means, the lock member 74 can reliably be kept in the locked condition or unlocked condition. In the alternative, if the guide groove is formed short in length, namely, starting at the positioning groove for the locked condition and ending at the area short of the positioning groove for the unlocked condition instead of ending at the positioning groove for the unlocked condition, the locking operation can be conducted more reliably. In case the guide groove is configured to have such a short length as just mentioned, the positioning member is required to climb over the side wall of the guide groove in order to move to the positioning groove for the unlocked position. Therefore, even if it should happen that the positioning member is not completely fitted to the positioning groove for the locked position due to erroneous operation or the like, an unlocked condition would not be resulted abruptly. Since this condition is not a locked condition, the artificial leg wearer can realize that a locked condition is not yet achieved. Therefore, the wearer can perform the locking operation once again before an unlocked condition is realized, so that a locked condition can reliably be achieved.

Figure 4:
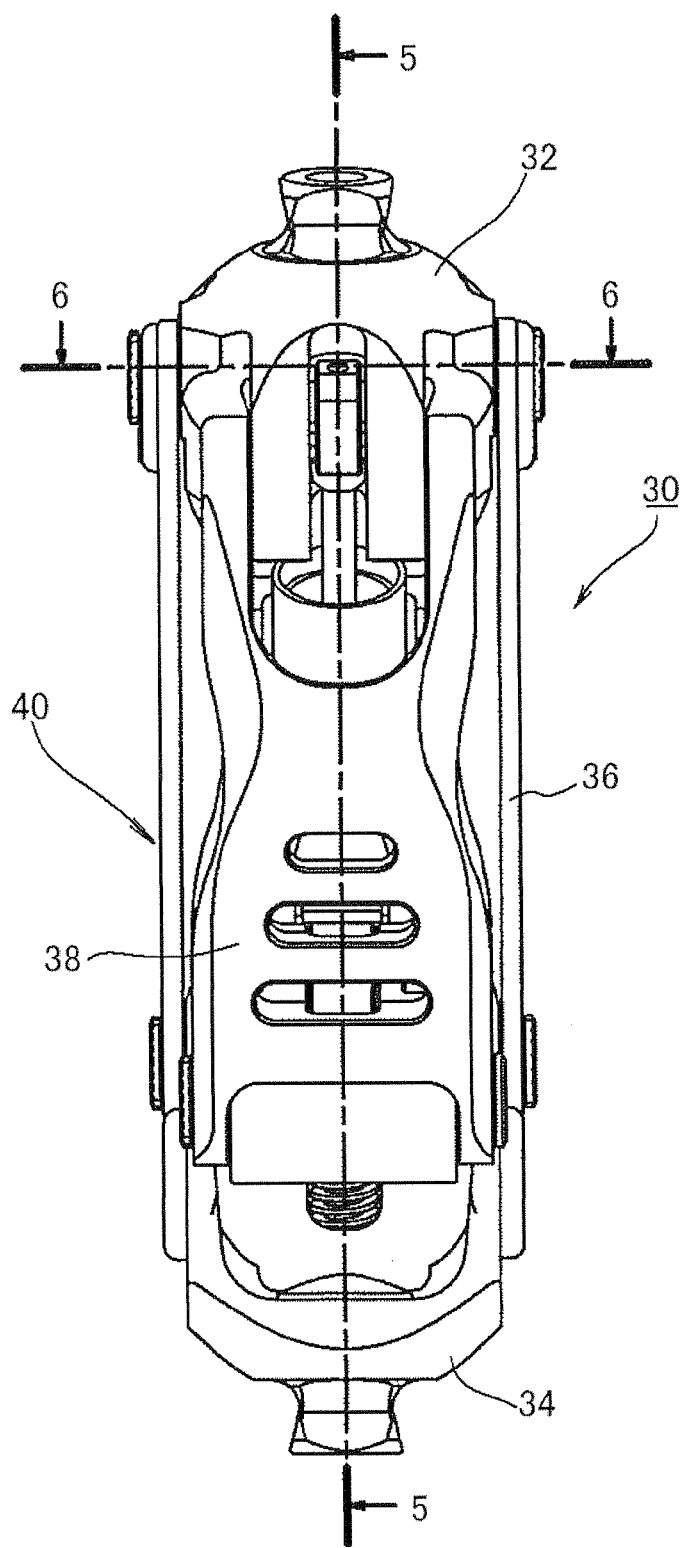
FIG. 4 is a front view showing another state of the knee joint of the first embodiment.
Figure 5:
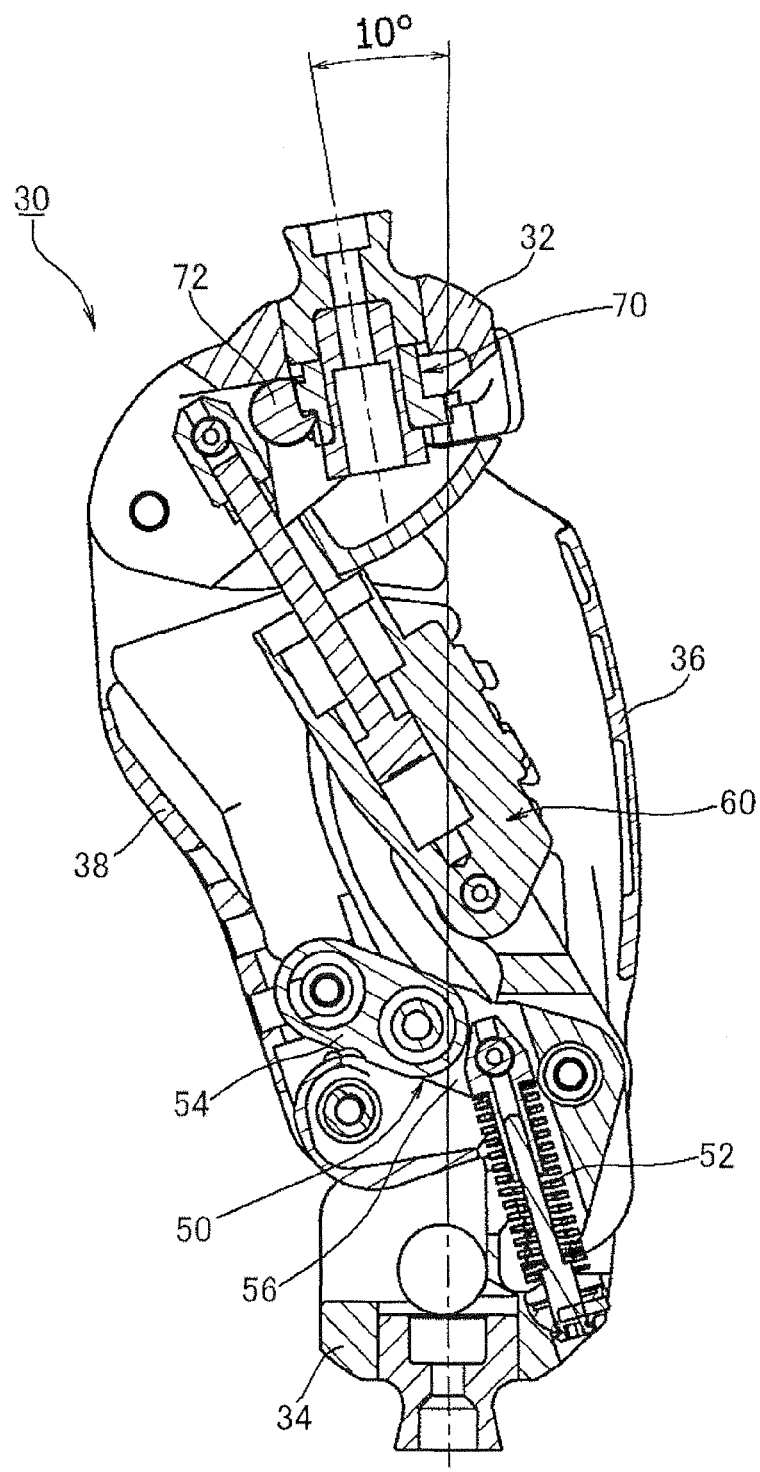
FIG. 5 is a sectional view taken on line 5-5 of FIG. 4.
Figure 6:
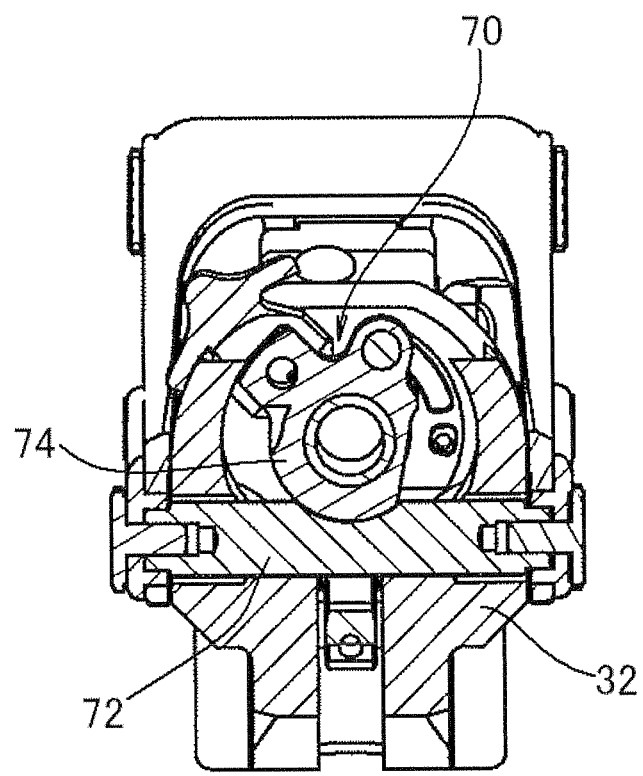
FIG. 6 is a sectional view taken on line 6-6 of FIG. 4.

When locked, the lock part 74L of the lock member 74 contacts the first plane 721 of the irregular part 720 on the oscillating shaft 72 side and so, the motion for bending the knee can be suppressed. That is, rotation of the oscillating shaft 72 in the direction for pushing the first plate 721 on the oscillating shaft 72 side and the end face on the lock member 74 side each other can reliably be prevented. However, the lock member 74 does not prevent the end face from moving in the opposite direction away from the first plane 721. The oscillating shaft 72 can move in the opposite direction until the second plane 722 is restricted. Since the knee joint 30 includes the extension assisting mechanism 50, a stance flexion or bouncing of about 10° of the knee angle can be attained as shown in FIGS. 4 through 6. Therefore, when compared with a case where a complete locked condition is realized, walking with a natural posture can be enjoyed without jeopardizing stability at walk on a snow-covered road or an uneven ground.

Figure 7:
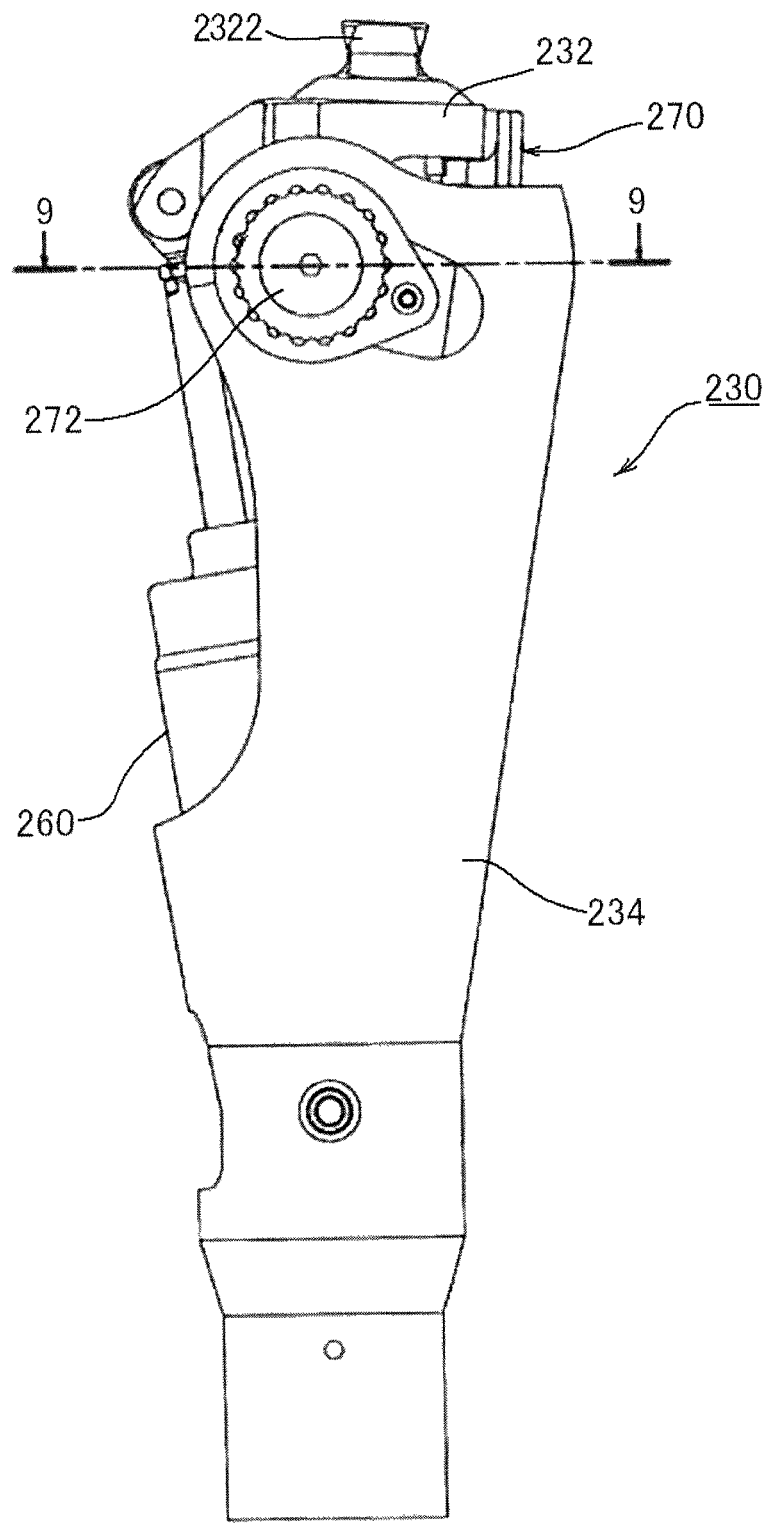
FIG. 7 is a front view showing a second embodiment of a knee joint according to the present invention.
Figure 8:
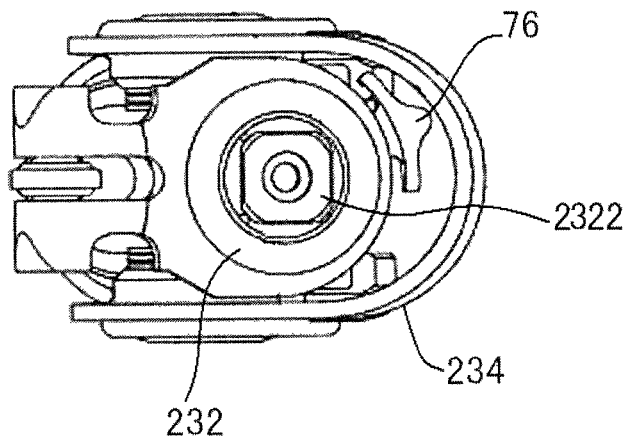
FIG. 8 is a sectional view taken on line 8-8 of FIG. 7.
Figure 9:
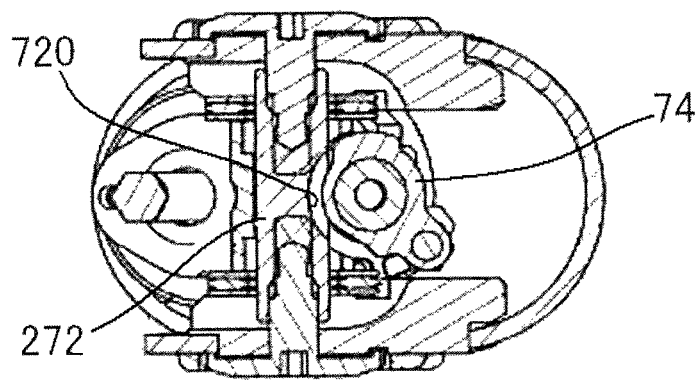
FIG. 9 is a sectional view taken on line 9-9 of FIG. 7.

FIGS. 7 through 9 show a second embodiment in which the present invention is applied to a knee joint having a single axis. The knee joint 230 of the second embodiment comprises an upper member 232 including an alignment block 2322, a lower member 234 chiefly composed of a hollow frame, and a single oscillating shaft (single axis) for swingably coupling the upper member 232 and the lower member 234. A resistance force (or a drag) generating means of the knee joint 230 is a pneumatic cylinder 260. A manual lock mechanism 270 in the knee joint 230 restricts the movement of the oscillating shaft 272 located at an upper part of the lower member 234. Therefore, the manual lock mechanism 270 is similar to the manual lock mechanism 70 in the first embodiment and comprised of an oscillating shaft 272 including an irregular part 720 and a lock member 74 rotatably supported by the alignment block 322 part and including a lever 76 for rotating operation.

Figure 10:
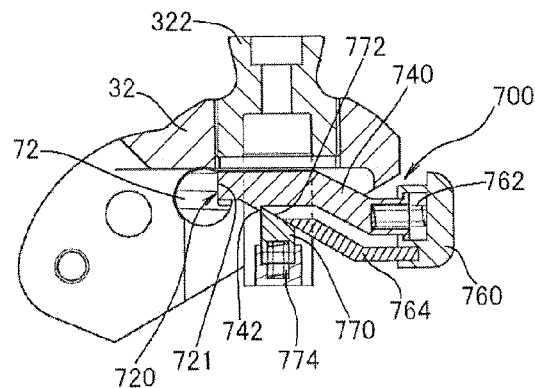
FIG. 10 is a sectional view showing a locked condition in another example of a manual lock mechanism according to the present invention.
Figure 11:
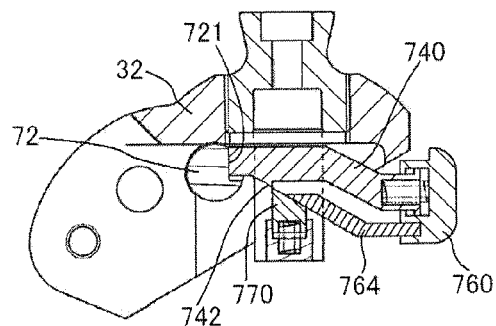
FIG. 11 is a sectional view showing a state when switching operation of the manual lock mechanism of FIG. 10 is made.
Figure 12:
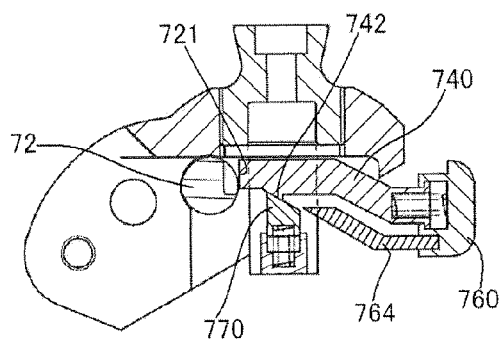
FIG. 12 is a sectional view showing an unlocked condition of the manual lock mechanism of FIG. 10.

FIGS. 10 through 12 show different states of another example of the manual lock mechanism. In the manual lock mechanism mentioned previously, a locked/unlocked condition can be switched by rotating operation of the lock member 74. In contrast, in a manual lock mechanism 700 shown in FIGS. 10 through 12, a locked/unlocked condition can be switched by sliding operation of the lock member 740. Longitudinal one end of the lock member 740 is caused to contact and separate from the first plane 721 of the irregular part 720 in accordance with sliding operation.

The lock member 740 includes a push-button type manual operating part 760 at the opposite side end part. A presser spring 762 is built in the manual operating part 760. The lock member 740 integrally supports a stopper interlocking plate 764 extending in parallel therewith. The lock member 740 is provided with a lock pawl 742. A stopper 770 including an upper inclination surface 772 is disposed at a lower part of the lock pawl 742. The stopper 770 is subject to a push-up force caused by the presser spring 774. The condition where the stopper 770 is caught by the lock pawl 742 (FIG. 10) is the locked condition. When the manual operating part 760 is pushed in order to switch from the locked condition to the unlocked condition, the stopper interlocking plate 764 pushes the stopper 770 downward through the upper inclination surface 772 and the stopper 770 is disengaged from the lock pawl 742 (FIG. 11). Though not shown, a spring force Fc for exerting force in a direction returning to the unlocked condition is applied to the lock member 740. The spring force Fc is set smaller than a spring force Fa of the presser spring 762 of the manual operating part 760 and a spring force Fb caused by the presser spring 774 of the stopper 770 (for example, spring force Fa>spring force Fb≧spring force Fc). Owing to this arrangement, when the hand is removed from the manual operating part 760, the lock member 740 whose lock pawl 742 is disengaged from the stopper 770 is brought into the unlocked condition where one end of the lock member 740 is separated from the oscillating shaft 72 (FIG. 12). For switching from the unlocked condition to the locked condition, the manual operating part 760 may simply be pushed in. In accordance with the push-in operation of the manual operation part 760, the lock pawl 742 of the lock member 740 is caught by the stopper 770.

The invention claimed is:

1. A knee joint for an artificial leg including a mechanical lock mechanism comprising:
    an upper member located at an upper side of the knee;
    a lower member located at a lower side of the knee;
    a coupling means including at least one oscillating shaft rotatably supported by one of said upper and lower members and adapted to couple said upper and lower members; and
    a manual lock mechanism capable of manually switching over oscillating motion of said upper and lower members between a locked condition and an unlocked condition when the knee is in an extended condition;
    wherein:
    (A) said manual lock mechanism comprises said oscillating shaft, which comprises an irregular part extending in an axial direction thereof;
    (B) said manual lock mechanism includes a lock member supported by one of said upper and lower members by which said oscillating shaft is rotatably supported, and said lock member can be manually selectively switched over between a locked condition of being in contact with said irregular part and an unlocked condition of being separate from said irregular part; and
    (C) said lock member extends in a longitudinal direction and is in face-to-face contact with said irregular part in the locked condition so that said upper and lower member prevent the knee from bending, and thereby force from said oscillating shaft and the direct load of a wearer of the artificial leg are applied as a longitudinal compression load to said lock member when the locked condition is kept.

2. The knee joint of claim 1, wherein said coupling means has either a single axis where the center of oscillation is constant, or a multi-axis where the center of oscillation is changed when said upper and lower member are in an oscillating condition.

3. The knee joint of claim 1, wherein said extended condition of the knee is in a range of knee angles from 0° where said upper and lower members are extended straight to 20° where no difficulty is felt for walking.

4. The knee joint of claim 1, wherein said irregular part is formed by digging out an outer peripheral side surface of said oscillating shaft having a circular shape in section and includes a first plane spreading in the same direction as a plane of said lock member's extension in the longitudinal direction and a second plane spreading in the direction crossing said first plane.

5. The knee joint of claim 4, wherein said lock member is rotatably supported by said upper member and said first plane has an arcuate shape.

6. The knee joint of claim 1, wherein said lock member is provided with a manual operating part opposite to said lock member's extension in the longitudinal direction when viewed in the longitudinal direction, and said manual operating part is located at an inner side of the contour of said knee joint.

7. The knee joint of claim 1, further comprising a position regulating means for positionally regulating said lock member in such a manner as to keep the locked condition when said lock member is in the locked condition.

8. An artificial thigh comprising the knee joint of claim 1, wherein said upper member includes a socket attaching part for attaching a socket and said lower member includes a foot part attaching part for attaching a foot part; and said lock member is rotatably supported around a supporting bolt that is one of the component elements of said socket attaching part.

9. The artificial thigh of claim 8, wherein said lock member is provided with a manual operating part opposite to said lock member's extension in the longitudinal direction when viewed in the longitudinal direction, and said manual operating part is positioned at such a height that the artificial thigh wearer can operate said manual operating part by himself.

10. The artificial thigh of claim 8, wherein said lock member can be switched over between said locked condition and said unlocked condition by either rotating operation or sliding operation.

11. The artificial thigh of claim 8 further comprising a resistance force generating means for generating a resistance force against the bending movement or extending movement of the knee caused by said knee joint, and said resistance force generating means and said manual lock mechanism are located at an inner side of the contour of said knee joint.

12. The artificial thigh of claim 11, wherein said resistance force generating means is any one of a hydraulic cylinder, a spring cylinder and a pneumatic cylinder.

* * * * *